United States Patent [19]
Knetsch

[11] Patent Number: 4,892,112
[45] Date of Patent: Jan. 9, 1990

[54] HAND TOOL FOR CLEANING DISINFECTING AND/OR LUBRICATING

[75] Inventor: Wilfried Knetsch, Vienna, Austria

[73] Assignee: Ogussa Osterreichische Gold-und Siber Scheideanstalt Scheid und Roessler Gessellschaft M.b.H. & Co. KG, Vienna, Austria

[21] Appl. No.: 229,056

[22] Filed: Aug. 5, 1988

[30] Foreign Application Priority Data

Aug. 7, 1987 [AT] Austria ............................... A2000/87

[51] Int. Cl.$^4$ ........................... B08B 3/02; B08B 9/00
[52] U.S. Cl. ................................... 134/102; 118/302; 118/317; 134/169 R; 137/240; 239/305; 239/333; 239/390
[58] Field of Search ............... 134/102, 168 R, 168 C, 134/169 R, 169 C; 118/302, 317; 239/305, 331, 333, 368, 390; 137/238, 240; 222/135

[56] References Cited

U.S. PATENT DOCUMENTS

| | | | |
|---|---|---|---|
| 2,201,080 | 5/1940 | Clark | 134/102 X |
| 2,420,109 | 5/1947 | Thompson | 239/331 X |
| 2,647,526 | 8/1953 | Casady et al. | 134/169 R X |
| 2,959,358 | 11/1960 | Vork | 239/333 X |
| 3,625,231 | 12/1971 | Littrell, Jr. | 134/102 |
| 3,811,408 | 5/1974 | Thompson | 134/166 C X |

FOREIGN PATENT DOCUMENTS

75879 11/1932 Sweden ............................... 134/102

Primary Examiner—Philip R. Coe
Attorney, Agent, or Firm—Seidel, Gonda, Lavorgna & Monaco

[57] ABSTRACT

The invention relates to a hand tool for the care of dental instruments which is connectable at its inlet to a pressurized gas source and at its outlet to the inlet sleeve of the dental instrument to be serviced, which hand tool is provided with at least one container for receiving the agent and connected to the presurized gas line leading form the inlet to the outlet of the hand tool. It is the object of the invention to permit a troublefree metering in of even highly viscous agents for the care of the instrument and the dispensing of various amounts of the agents. This object is achieved by providing a pressure control valve from which a pressurized gas line leads to the outlet of the hand tool downstream of the inlet of the hand tool and by providing at least one pump for conveying the agent, the intake line of the pump being connected with the at least one container for receiving the agent and the pressure line being connected with the pressurized gas line leading to the outlet of the hand tool in a site downstream of the pressure control valve and upstream of the outlet of the hand tool.

6 Claims, 3 Drawing Sheets

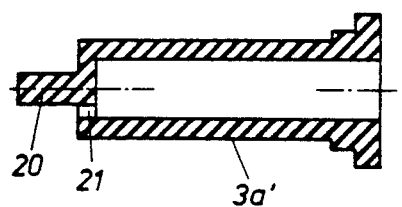
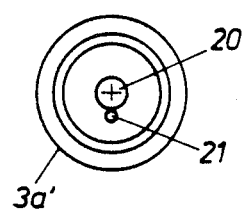
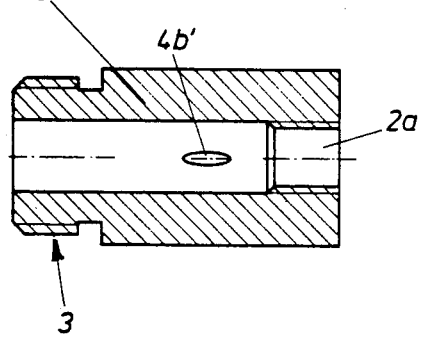
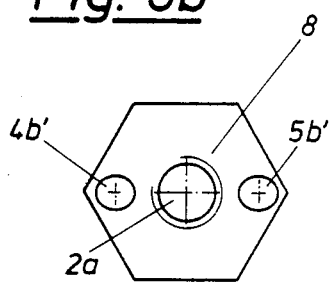
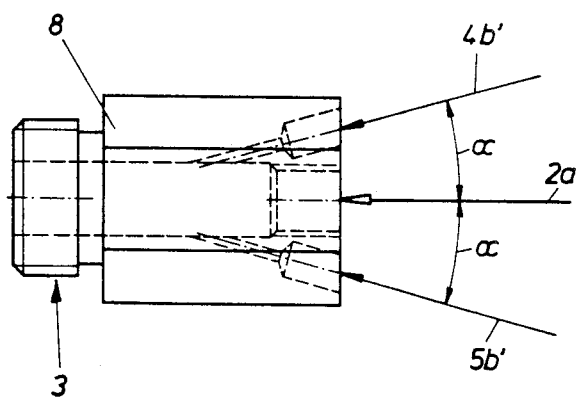

HAND TOOL FOR CLEANING DISINFECTING AND/OR LUBRICATING

The present invention relates to a hand tool for the cleaning and/or disinfecting and/or lubricating of dental tool holders or angle pieces or turbine angle pieces or the like which is attachable on its inlet to a source of pressurized gas or preferably compressed air which can be turned on and off, in particular to the dental unit provided in each dental practice and which is connectable on its outlet to the inlet sleeve of the dental tool holder or angle piece or turbine angle piece to be cleaned and/or disinfected and/or lubricated, which hand tool is provided with at least one container for receiving the cleaning and/or disinfecting and/or lubricating agent, which container is connected to the pressurized gas line extending from the inlet to the outlet of the hand tool. A hand tool of this type is known from U.S. Pat. No. 3 811 408. This known hand tool, however, requires complicated handling and difficulties arise in the metering in of the cleaning and/or disinfecting and/or lubricating agent, in particular because agents of higher viscosity cannot be used. Lubricants of higher viscosity, however, would be particularly valuable for this purpose, because they would remain in the dental tool holder or angle piece or turbine angle piece or the like, which are designated as dental instruments for short in the following, for extended periods and would assure long-term lubrication. This fact is particularly essential for such dental instruments in view of the very high rotating speeds to which they are subjected (as an example, an angle piece with built-in transmission heats up during operation due to the high number of revolutions per minute, so that the lubrication of such an angle piece must meet particularly high requirements).

Moreover, the known hand tool allows only the metering in of very small amounts of agents for its servicing at one time; these small amounts may be adequate for the lubrication of the dental instrument, but larger amounts are necessary for a proper cleaning and disinfection.

It is the object of the invention to eliminate these disadvantages of the known hand tool. This is achieved according to the invention in the hand tool initially mentioned by providing a pressure control (safety) valve downstream of the inlet of the hand tool from which valve a pressurized gas line leads to the outlet of the hand tool, at least one preferably manually actuated pump being provided for conveying the cleaning and/or disinfecting and/or lubricating agent, the intake line of the pump being connected to the at least one container for receiving the cleaning and/or disinfecting and/or lubricating agent, while the pressure line of the pump is connected to the pressurized gas line leading to the outlet of the hand tool at a site downstream from the pressure control valve and upstream of the outlet of the hand tool. It is particularly advantageous according to a further development of the invention to use a reciprocating pump with two nonreturn valves of which one is provided in the intake line and the other in the pressure line.

It is further of advantage if the connecting site of the pressure line of the pump with the pressurized gas line leading to the outlet of the hand tool is provided immediately upstream of the outlet of the hand tool, the junction of the pressure line with the pressurized gas line leading to the outlet of the hand tool being provided at an angle of about 15 degrees in relation to the axis of said pressurized gas line. The connecting tube, in particular the turbine tube, of the dental unit is conveniently connectable to the inlet of the hand tool by means of a quick-turn coupling known per see.

Sealing of the dental instrument to be serviced against the hand tool can be provided according to a further development of the invention by providing a cylindrical connecting sleeve consisting of an elastic material resistant to the cleaning and/or disinfecting and/or lubricating agent, preferably of silicone rubber or silicone plastics, onto which sleeve the tool holder or angle piece or turbine angle piece to be cleaned and/or disinfected and/or lubricated is slidable or pluggable. If necessary, the connecting sleeve can be only partly open on its front end in order to cover the channels provided for conveying a water-air-mixture in the tool holder or angle piece or turbine angle piece. This measure allows the abutment of the elastic outer wall of the connecting sleeve against the inner wall of the sleeve-like connecting end and thus the required seal of the connection between dental instrument and connecting sleeve of the tool holder as a result of the backpressure of the pressurized gas charged with the agent building up in the interior of the dental instrument pluggable with its sleeve-like connecting end onto the elastic connecting sleeve of the hand tool.

The invention in particular permits the use of highly viscous agents for the care of the tool, preferably lubricants and a safe and troublefree metering in of even larger amounts of agents, in particular of cleaning and disinfecting agents, and the service operation to be carried out quickly and without problems by means of the dental unit provided in each dental practice. This results in a prolonged service life of the dental instruments.

The invention is desribed in detail in the following by means of an exemplary embodiment of the hand tool according to the invention under reference to the accompanying drawings wherein FIG. 1 shows a partially sectional elevational view of the hand tool according to the invention;

FIG. 5a shows a second embodiment of such a connecting sleeve in longitudinal section and FIG. 5b shows a front view thereof;

Figure 1:
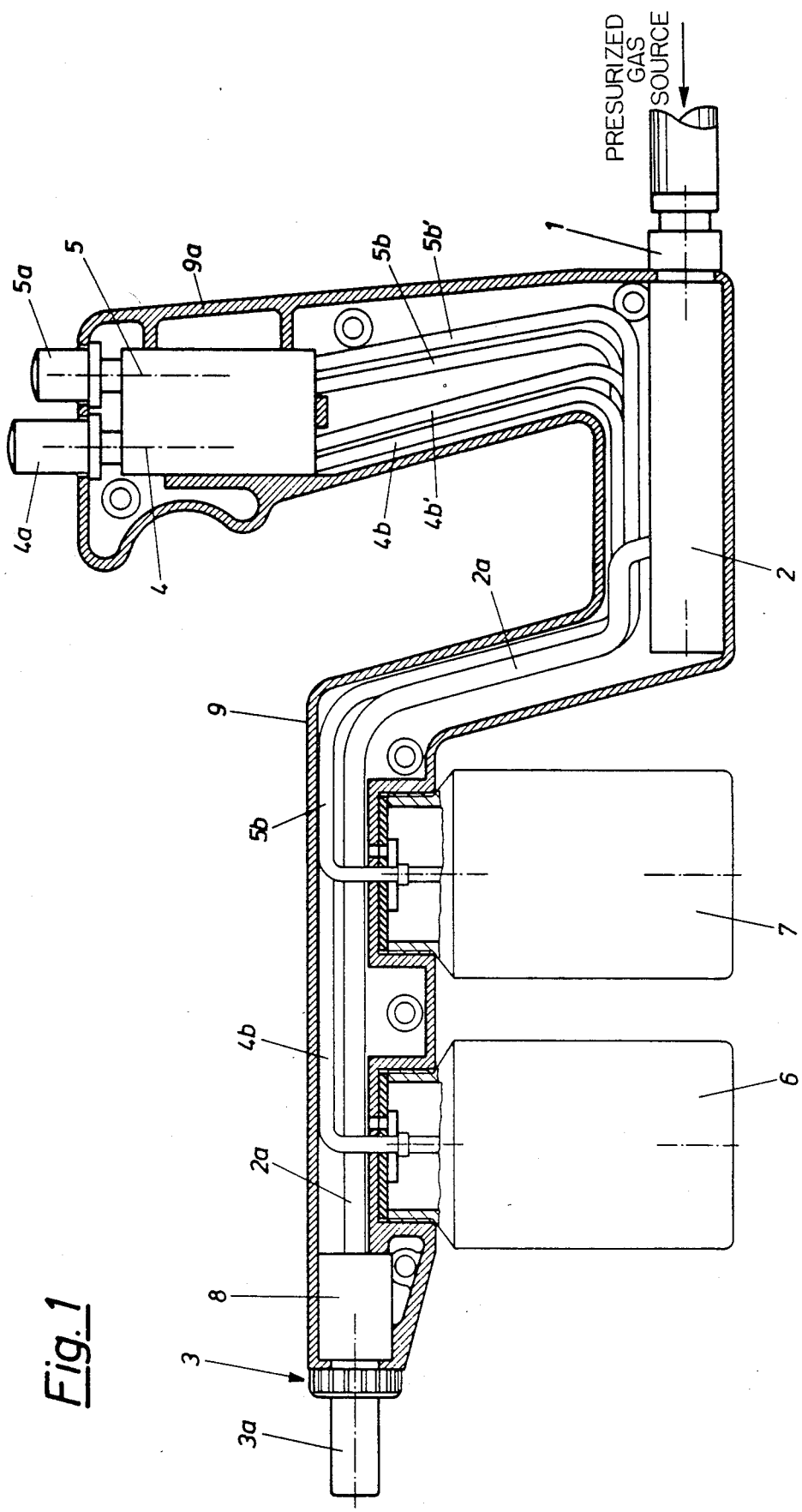

FIG. 6a shows a longitudinal section of the metering or mixing chamber of the hand tool according to the invention and FIG. 6b shows a rear view of said chamber, while FIG. 6c shows a top plan view of said chamber. p FIG. 1 shows the hand tool according to the invention in its entity. A pressurized gas source, preferably the dental unit provided in each dental practice, is connected at the inlet 1 of the hand tool. The tool is plugged onto the turbine tube in place of the turbine angle piece by means of the provided quick-turn coupling, if no such coupling is provided, it is screwed onto the thread of the tube. On actuating the foot pedal of the dental unit, namely on turning on the turbine angle piece not present now, air is introduced into the hand tool with the flow pressure adjusted for the turbine of normally about 2.2 bar. A presssure control (safety) valve 2 reduces this pressure to about 1 bar without subjecting the tubes of the dental unit to stress. The compressed air is now further conveyed through the pressurized gas line 2a to the outlet 3 where turbine angle pieces and tool holders and angle pieces of the most diverse kinds (not represented), termed dental instruments for short in the following, can be plugged on by means of exchangeable and sealing adapters, for instance the elastic connecting sleeves 3a and 3a' sketched in FIG. 1 and represented in FIG. 4a,b and 5a,b.

The hand tool shown in FIG. 1 is provided with two storage containers 6,7 for cleaning (disinfecting) and lubricating agents from which these cleaning (disinfecting) and lubricating agents, called agents for short in the following, are sucked via intake lines 4b, 5b by means of two manually actuated (pushbuttons 4a, 5a) reciprocating pumps 4,5 and can be injected under pressure independently of one another into the pressurized gas line 2a so that the pressurized gas charges the agents into the dental instrument plugged on. For this purpose, a pressure line 4b', 5b' emanates from each pump 4,5 and terminates together with the pressurized gas line 2a in a metering or mixing chamber 8 (c.f. also FIG. 6a,b,c) disposed in flowing direction upstream of the outlet 3, but downstream of the pressure control valve 2. Associated with each pump 4,5 are two nonreturn valves 4', 4" and 5', 5" shown in FIG. 2, in which the nonreturn valves 4'5' are disposed in the intake lines 4b and 5b leading to the containers 6 and 7 and the nonreturn valves 4", 5" are dispoed in the pressure lines 4b' and 5b' leading to the mixing chamber 8. The pressure by which the metering of the agents in the mixing chamber 8 is effected and which must be exerted by the pumps 4,5 is higher than the pressure in the pressure line 2a, but lower than the pressure acting at the inlet 1 of the hand tool and amounts to e.g. about 1.2 bar.

The compressed air discharged from the outlet 3 of the hand tool and charged with the agents penetrates the dental instrument (not represented) plugged onto the connecting sleeve 3a and is discharged again at the point of the instrument. If the pumps 4 and 5 are not actuated, but the foot pedal of the dental unit remains actuated, excess amounts of liquid can be evacuated from the dental instruments by the uncharged compressed air so that they are not conveyed into the mouth of the patient or into a possibly provided electric drive motor.

Figure 2:
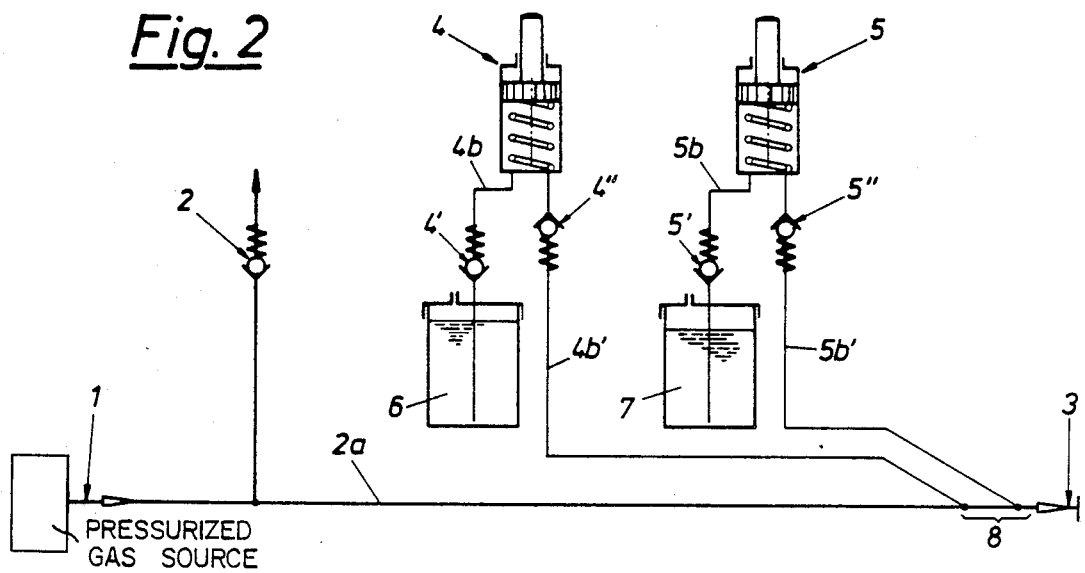
FIG. 2 shows a basic representation of the functional elements of the hand tool according to the invention.

The mixing ratios of the agents contained in the containers 6,7 with the compressed air can be regulated and adjusted to the respective requirements by the number of actuations of the reciprocating pumps 4,5 (c.f. FIG. 2) by means of the pushbuttons 4a, 5a (c.f. FIG. 1). Since the agents are conveyed by means of pumps, any type and viscosity of the agents is possible.

All parts of the hand tool are disposed on an angled, elongated housing 9 with a handle-like projection 9a.

Figure 3:
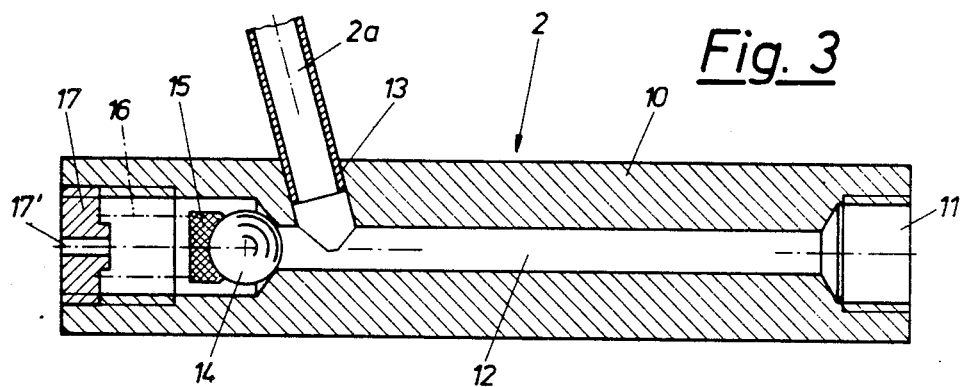
FIG. 3 shows a longitudinal section of the pressure control valve.

FIG. 3 shows an embodiment of the pressure control valve 2, one end of the valve body 10 provided with an internal longitudinal bore 12 being provided with a connecting thread 11 for the turbine tube quick-turn coupling. At 13, the pressurized gas line 2a leading to the outlet 3 of the hand tool and optionally consisting of a PVC tube is inserted, preferably glued, into the valve body 10. A valve ball 14, with interposition of a pad 15 of foamed plastic material for noise damming and biassed by a pressure spring 16, is used to close off the longitudinal bore 12; on its other end, the pressure spring 16 is supported on a screw lid 17 with ventilation bore 17' closing off a axial cavity in the valve body 10 receiving the ball 14 and the pressure spring 16.

Figure 4A:
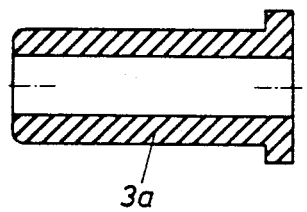
FIG. 4a shows a longitudinal section of a first embodiment of the connecting sleeve at the outlet of the hand tool according to the invention and FIG. 4b shows a front view of this connecting sleeve.
Figure 4B:
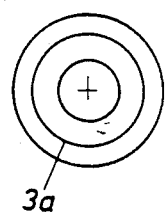

FIG. 4a,b and 5a,b show two examples of connecting sleeves 3a, 3a' made of an elastic material resistant to the agents, preferably silicone rubber or silicone India rubber. The connecting sleeve 3a shown in FIG. 4a and 4b is suitable for tool holders and angle pieces of all brands and types. The connecting sleeve 3a' shown in FIG. 5a and 5b is mainly suitable for W & H turbine angle pieces with Rotoquick connection, the passage opening being provided with a nose-like end 20 in front to prevent the agent from penetrating into the spraying channel of the drill or hand tool; a small, excentrically disposed bore 21 is is provided in the front wall for the discharge of the compressed air charged with agent.

Sealing of the outlet 3 of the hand tool against the dental instrument to be serviced is achieved by the elastic connecting sleeves 3a, 3a' expanding under pressure and sealingly abutting the inner wall of the plugged-on dental instrument.

FIG. 6a, 6b and 6c show the mixing chamber 8 of the hand tool in detail. FIG. 6c, which constitutes a horizontal projection of FIG. 1, shows particularly clearly that the pressure lines 4b' and 5b' of the pumps 4,5 each terminate in the mixing chamber 8 at an acute angle $\alpha$ of about 15 degrees in relation to the pressurized gas line 2a disposed in the longitudinal axis. This permits an optimal charging of the compressed carrier air with the agents. Due to the otherwise parallel arrangement of the lines 2a, 4b' and 5b' in the hand tool, only line 2a is represented in FIG. 1. The mixing chamber 8 has a hexagonal outer circumference (FIG. 6b) and is provided with appropriate connecting threads.

The hand tool according to the invention can be provided without difficulty with three storage containers for cleaning, disinfecing and lubricating agents and three pumps.

Instead of using the hand tool according to the invention together with a dental unit, it would also be possible to use the same principle for providing a larger facility for several instruments with automatic operation and individual air supply.

I claim:

1. A hand tool for cleaning, disinfecting, and/or lubricating dental tool holders, angle pieces, turbine pieces, or the like, said tool comprising:
   (a) an inlet opening,
   (b) a source of pressurized gas connected to said hand tool inlet opening,
   (c) means for initiating and terminating the flow of said source of pressurized gas into said hand tool inlet opening,
   (d) an outlet opening comprising means for mounting a dental tool holder, an angle piece, a turbine piece or the like thereon,
   (e) a pressure control valve comprising an upstream portion and a downstream portion, wherein said pressure control valve upstream portion is in open communication with said hand tool inlet opening, said pressure control valve being located downstream of said hand tool inlet opening,
   (f) a pressurized gas line which is in open communication, at one end, with said pressure control valve downstream portion, and said pressurized gas line being in open communication at the other end with said hand tool outlet opening, (g) a container defining a cavity for receiving an agent for cleaning, disinfecting and/or lubricating the dental holder, angle piece, turbine piece, or the like mounted on said hand tool outlet opening, and (h) at least one pump means for conveying said agent from said container to said hand tool outlet opening, wherein the upstream end of said pump means comprises a first conduit which is in open communication with the cavity of said container and wherein the downstream end of said pump means comprises a second conduit which is in open communication with said pressurized gas line.

2. A hand tool in accordance with claim 1 wherein said pump means comprises a reciprocating pump with two non-return valves one of which is disposed in said first conduit of said pump means and the other is disposed in said second conduit of said pump means.

3. A hand tool in accordance with claim 1 wherein said hand tool inlet opening is connected to said pressurized gas source by means of a quick-turn coupling.

4. A hand tool in accordance with claim 1 wherein said hand tool outlet opening comprises a cylindrical connecting sleeve made from an elastic material resistant to the agent contained in said container.

5. A hand tool for cleaning, disinfecting, and/or lubricating dental tool holders, angle pieces, turbine pieces, or the like, said tool comprising:

(a) an inlet opening, (b) a source of pressurized gas connected to said hand tool inlet opening, (c) means for initiating and terminating the flow of said source of pressurized gas into said hand tool inlet opening, (d) an outlet opening comprising means for mounting a dental tool holder, an angle piece, a turbine piece or the like thereon, (e) a pressure control valve comprising an upstream portion and a downstream portion, wherein said pressure control valve upstream portion is in open communication with said hand tool inlet opening, said pressure control valve being located downstream of said hand tool inlet opening, (f) a hollow junction means located upstream of said hand tool outlet opening, said junction means having an upstream opening and a downstream opening, wherein said junction means downstream opening is in open communication with said hand tool outlet opening, (g) a pressurized gas line which is in open communication at one end with said pressure control valve downstream portion and in open communication at the other end with said junction means upstream opening, (h) a container defining a cavity for receiving an agent for cleaning, disinfecting and/or lubricating the dental holder, angle piece, turbine piece, or the like mounted on said hand tool outlet opening, and (i) at least one pump means for conveying said agent from said container to said hand tool outlet opening, wherein the upstream end of said pump means comprises a first conduit which is in open communication with the cavity of said container and wherein the downstream end of said pump means comprises a second conduit which is in open communication with said junction means upstream opening.

6. A hand tool in accordance with claim 5 wherein said pressurized gas line enters into said junction means upstream opening along the longitudinal axis of said junction means and wherein said pump means second conduit enters into said junction means upstream opening at an angle of about 15° in relation to the longitudinal axis of said junction means.

* * * * *